(12) United States Patent
Sahasranaman et al.

(10) Patent No.: US 12,026,275 B2
(45) Date of Patent: Jul. 2, 2024

(54) SYSTEMS AND METHODS FOR SEMANTIC CONTEXT ENRICHMENT AND DATA MASKING

(71) Applicant: MicroStrategy Incorporated, Tysons Corner, VA (US)

(72) Inventors: Tejas Sahasranaman, Fairfax, VA (US); Nida Imtiaz, Vienna, VA (US); Siyuan Fan, Falls Church, VA (US); Xiuyi Ye, Fairfax, VA (US)

(73) Assignee: MicroStrategy Incorporated, Tysons Corner (VA)

( * ) Notice: Subject to any disclaimer, the term of this patent is extended or adjusted under 35 U.S.C. 154(b) by 177 days.

(21) Appl. No.: 17/191,976

(22) Filed: Mar. 4, 2021

(65) Prior Publication Data
US 2021/0279362 A1    Sep. 9, 2021

Related U.S. Application Data

(60) Provisional application No. 62/985,425, filed on Mar. 5, 2020.

(51) Int. Cl.
| | | |
|---|---|---|
| *G06F 21/62* | (2013.01) |
| *G06F 21/31* | (2013.01) |
| *G06Q 10/10* | (2023.01) |
| *G06Q 30/0201* | (2023.01) |
| *G06Q 50/26* | (2012.01) |
| *G16H 10/60* | (2018.01) |

(52) U.S. Cl.
CPC .......... *G06F 21/6245* (2013.01); *G06F 21/31* (2013.01); *G06Q 10/10* (2013.01); *G06Q 30/0201* (2013.01); *G06Q 50/265* (2013.01); *G16H 10/60* (2018.01)

(58) Field of Classification Search
CPC .... G06F 21/6245; G06F 21/31; G06F 16/951; G16H 10/60; G16H 10/10; G06Q 30/0201; G06Q 50/264
See application file for complete search history.

(56) References Cited

U.S. PATENT DOCUMENTS

| | | | |
|---|---|---|---|
| 10,438,264 B1 * | 10/2019 | Viswanathan | ......... G06F 16/951 |
| 2010/0161709 A1 * | 6/2010 | Fourman | ............... H04L 67/306 |
| | | | 709/203 |
| 2016/0103903 A1 * | 4/2016 | Vivalda | ................. H04L 65/403 |
| | | | 709/204 |
| 2017/0169030 A1 * | 6/2017 | Ben-Tzur | ............ G06F 16/9535 |
| 2018/0314853 A1 * | 11/2018 | Oliner | ................. G06F 21/6254 |
| 2021/0141838 A1 * | 5/2021 | Atallah | ............... G06F 16/9577 |

* cited by examiner

*Primary Examiner* — Meng Li
*Assistant Examiner* — Felicia Farrow
(74) *Attorney, Agent, or Firm* — Bookoff McAndews, PLLC

(57) ABSTRACT

In a method for electronic data card enhancements, at least one electronic data card may be requested containing data within a plurality of data elements. At least one value adding feature may be determined applicable to the data. Additionally, the at least one value adding feature may be applied to the data, and the at least one electronic data card may be presented containing data and the applied at least one value adding feature of the data.

20 Claims, 6 Drawing Sheets

SYSTEMS AND METHODS FOR SEMANTIC CONTEXT ENRICHMENT AND DATA MASKING

RELATED APPLICATION(S)

This application claims priority to U.S. Provisional Application No. 62/985,425 filed Mar. 5, 2020, the entire disclosure of which is hereby incorporated herein by reference in its entirety.

TECHNICAL FIELD

Various embodiments of the present disclosure relate generally to providing on demand contextually relevant information.

INTRODUCTION

Today electronic networks commonly contain more data than is possible for a user to efficiently digest. A user may utilize a search engine to look up data, but this may lead to confusion, as the user may not know what the returned data may represent without further contextual data. Furthermore, personal privacy is an important factor when data is being presented. Therefore it is important to only present data to users who are authorized to view said data and prevent personally identifiable information from being accessed by users who do not have permission to access those data.

The present disclosure is directed to addressing one or more of these challenges. The background description provided herein is for the purpose of generally presenting the context of the disclosure. Unless otherwise indicated herein, the materials described in this section are not prior art to the claims in this application and are not admitted to be prior art, or suggestions of the prior art, by inclusion in this section.

SUMMARY

According to certain aspects of the disclosure, non-transitory computer readable media, systems, and methods are disclosed for providing electronic data card enhancements. Each of the examples disclosed herein may include one or more of the features described in connection with any of the other disclosed examples.

In one example, a computer-implemented method may be used for electronic data card enhancements. The method may include requesting, by one or more processors, at least one electronic data card containing data within a plurality of data elements; determining, by the one or more processors, at least one value adding feature applicable to the data; applying, by the one or more processors, the at least one value adding feature to the data; and presenting, by the one or more processors, the at least one electronic data card containing data and the applied at least one value adding feature of the data.

According to another aspect of the disclosure, a computer system for electronic data card enhancements may include at least one memory having processor-readable instructions stored therein; and at least one processor configured to access the memory and execute the processor-readable instructions, which when executed by the processor configures the processor to perform a plurality of functions. The functions may include requesting at least one electronic data card containing data within a plurality of data elements; determining at least one value adding feature applicable to the data; applying the at least one value adding feature to the data; and presenting the at least one electronic data card containing data and the applied at least one value adding feature of the data.

According to still another aspect of the disclosure, a non-transitory computer-readable medium comprising instructions for electronic data card enhancements, the non-transitory computer-readable medium storing instructions that, when executed by at least one processor, may configure the at least one processor to perform requesting, by one or more processors, at least one electronic data card containing data within a plurality of data elements; determining, by the one or more processors, at least one value adding feature applicable to the data; applying, by the one or more processors, the at least one value adding feature to the data; and presenting, by the one or more processors, the at least one electronic data card containing data and the applied at least one value adding feature of the data.

Additional objects and advantages of the disclosed embodiments will be set forth in part in the description that follows, and in part will be apparent from the description, or may be learned by practice of the disclosed embodiments.

It is to be understood that both the foregoing general description and the following detailed description are exemplary and explanatory only, and are not restrictive of the disclosed embodiments, as claimed.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

FIGS. 4A and 4B depict exemplary user interfaces for a data masking feature, according to one aspect of the present disclosure.

DETAILED DESCRIPTION

Figure 1:
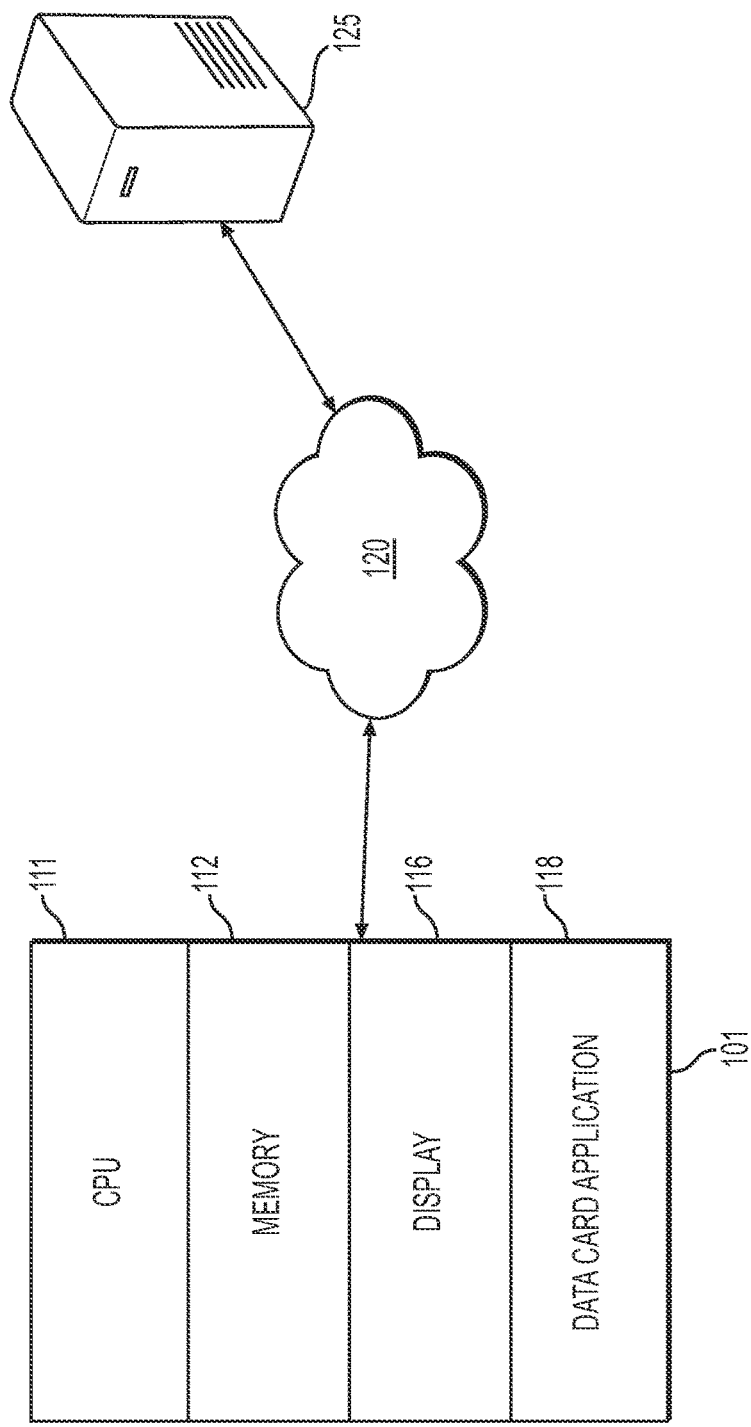
FIG. 1 depicts an exemplary environment in which systems, methods and other aspects of the present disclosure may be implemented.

The subject matter of the present description will now be described more fully hereinafter with reference to the accompanying drawings, which form a part thereof, and which show, by way of illustration, specific exemplary embodiments. An embodiment or implementation described herein as "exemplary" is not to be construed as preferred or advantageous, for example, over other embodiments or implementations; rather, it is intended to reflect or indicate that the embodiment(s) is/are "example" embodiment(s). Subject matter can be embodied in a variety of different forms and, therefore, covered or claimed subject matter is intended to be construed as not being limited to any exemplary embodiments set forth herein; exemplary embodiments are provided merely to be illustrative. Likewise, a reasonably broad scope for claimed or covered subject matter is intended. Among other things, for example, subject matter may be embodied as methods, devices, components, or systems. Accordingly, embodiments may, for example, take the form of hardware, software, firmware, or any combination thereof (other than software per se). The following detailed description is, therefore, not intended to be taken in a limiting sense.

Throughout the specification and claims, terms may have nuanced meanings suggested or implied in context beyond an explicitly stated meaning. Likewise, the phrase "in one embodiment" as used herein does not necessarily refer to the same embodiment and the phrase "in another embodiment" as used herein does not necessarily refer to a different embodiment. It is intended, for example, that claimed subject matter include combinations of exemplary embodiments in whole or in part.

The terminology used below may be interpreted in its broadest reasonable manner, even though it is being used in conjunction with a detailed description of certain specific examples of the present disclosure. Indeed, certain terms may even be emphasized below; however, any terminology intended to be interpreted in any restricted manner will be overtly and specifically defined as such in this Detailed Description section. Both the foregoing general description and the following detailed description are exemplary and explanatory only and are not restrictive of the features, as claimed.

In this disclosure, the term "based on" means "based at least in part on." The singular forms "a," "an," and "the" include plural referents unless the context dictates otherwise. The term "exemplary" is used in the sense of "example" rather than "ideal." The term "or" is meant to be inclusive and means either, any, several, or all of the listed items. The terms "comprises," "comprising," "includes," "including," or other variations thereof, are intended to cover a non-exclusive inclusion such that a process, method, or product that comprises a list of elements does not necessarily include only those elements, but may include other elements not expressly listed or inherent to such a process, method, article, or apparatus. Relative terms, such as, "substantially" and "generally," are used to indicate a possible variation of ±10% of a stated or understood value.

In the following description, embodiments will be described with reference to the accompany drawings. Various embodiments of the present disclosure relate generally to methods and systems for providing electronic data card enhancement features. For example, various embodiments of the present disclosure relate to providing contextual data by providing content enrichment and metric trending to electronic data cards. In some arrangements, data masking feature may be applied to the electronic data card for data protection related functions.

As described above, users searching for relevant information may be overwhelmed with the amount of information available. Often times the user may acquire data but have difficulties digesting the data without any contextual information to add meaning to the acquired data. For example, if the user acquires data on the revenue of a company, just the revenue data of the company may not provide the user with a sense of how the company is performing. By displaying contextual data such as the revenues of similar companies, the user may gain a better understanding of the health of the company. Therefore, a need exists to provide contextual data to the data acquired by the user so that the user may better understand the acquired data. Furthermore, a need exists to maintain private or sensitive user identifiable data and only display the private or sensitive data to users who has the permission or privileges to view such data.

Referring now to the appended drawings, FIG. 1 depicts an exemplary network environment 100 in which systems, methods and other aspects of the present disclosure may be implemented. Environment 100 may include the at least one user device 101 under the operation of a plurality of users, a network 120, and at least one server 125. The server 125 may act as a repository for information discoverable by the user of the user device 101. The server 125 may communicate to the user device 101 via a network 120. Such a network may be any suitable network or combination of networks and may support any appropriate protocol suitable for communication of data between various components in the system environment 100. The network 120 may include a public network (e.g., the Internet), a private network (e.g., a network within an organization), or a combination of public and/or private networks. The server 125 may be implemented using multiple computers that cooperate to perform the functions discussed below, which may be located remotely from each other.

The user device 101 may be operated by one or more users to perform electronic data card enhancement features. The user device 101 may include a central processing unit (CPU) 111, memory 112, display 116, and/or electronic data card application 118. The electronic data card application 118 may be executed by the CPU 111, and may also include one or more extensions installed on the application 118 that may provide additional features. Examples of user device 101 may include smartphones, wearable computing devices, tablet computers, laptops, and desktop computers.

Environment 100 may include one or more computer systems configured to gather, process, transmit, and/or receive data. In general, whenever document environment 100 are described as performing an operation of gathering, processing, transmitting, or receiving data, it is understood that such operation may be performed by a computer system thereof. In general, a computer system may include one or more computing devices, as described in connection with FIG. 5 below.

Figure 2:
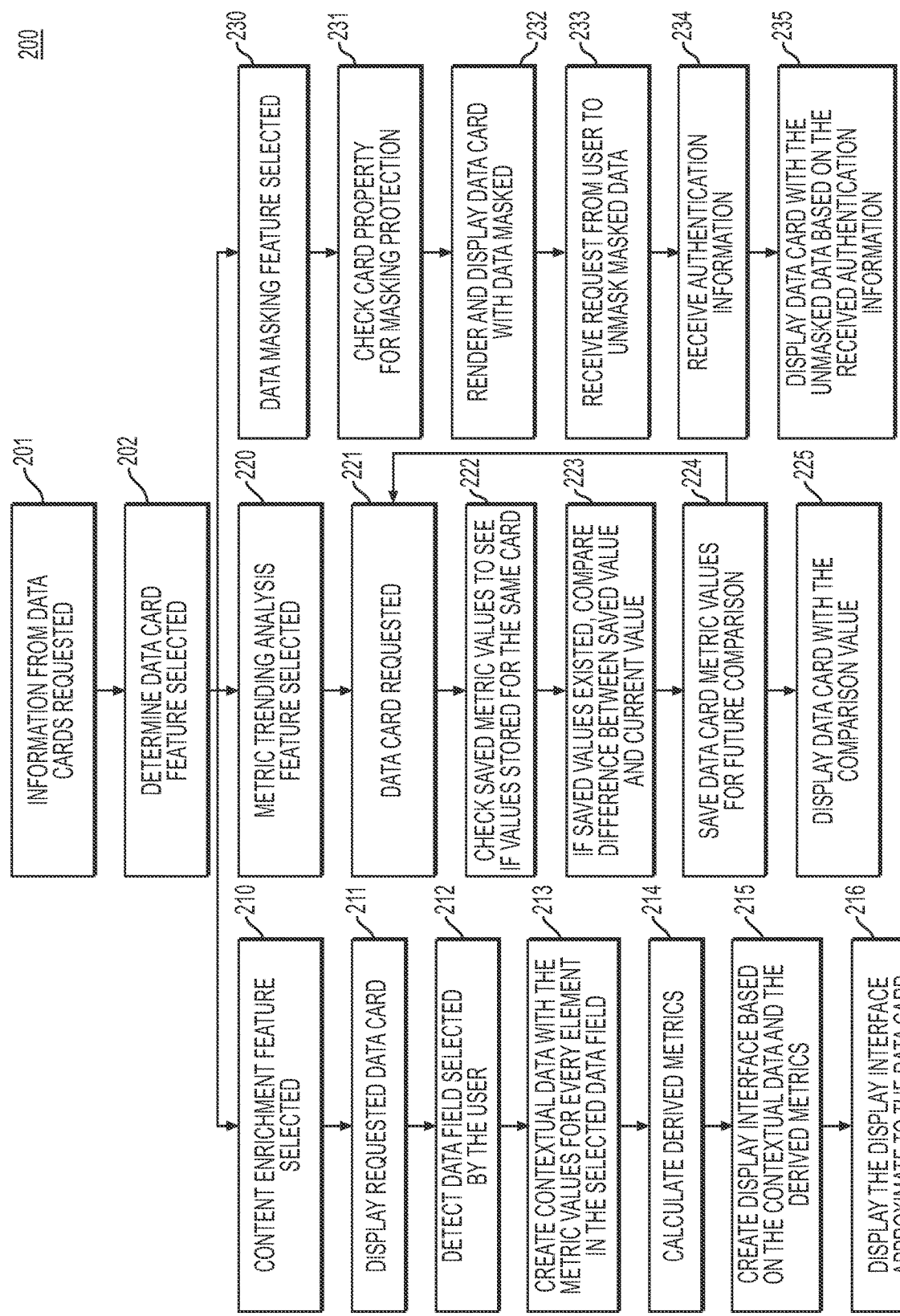
FIG. 2 depicts an exemplary flow diagram of electronic data card enhancement, according to one aspect of the present disclosure.

FIG. 2 depicts an exemplary flow diagram 200 of electronic data card enhancement, according to one aspect of the present disclosure. Exemplary electronic data cards are described in commonly assigned U.S. application Ser. No. 16/688,065, which is incorporated herein by reference in its entirety. Diagram 200 may begin with step 201 where information from electronic data cards may be requested. Information may be requested as part of a user request for electronic data cards. For example, the user may perform a search for a particular interest and an electronic data card may be returned to the user displaying information regarding the particular interest. Alternatively, information may be requested directly by the user and separately from the user request for the electronic data card. At step 202 an electronic data card enhancement feature to be applied to the electronic data card may be determined based on the requested information from the electronic data cards.

At step 210, the content enrichment feature may be requested, for example by a user, to be applied to the information contained in the electronic data cards. At step 211, a user requested electronic data card may be displayed to the user on the user device 101, which may correspond to the information requested in step 201. At step 212, a user selection of data fields on the user requested electronic data card may be detected. The user may select the data fields by moving a pointing device (e.g., a mouse, a finger) over the data fields or by performing a gesture (e.g., touching, clicking) on the data fields. The data fields may contain elements such as key performance indicators (KPI), and/or other metrics values displayed on the electronic data card. Upon detecting the selection of the data fields, at step 213 contextual data may be created using the metrics values associated with the selected data field on the electronic data card. The contextual data may be created via a software call to an application programing interface (API) of a software library. The software call may also include the metric values from the selected data field to the software library so that the contextual data may correspond to the metrics values. In another embodiment, upon receiving the software call, the library may request the metric values associated with the selected data field to create the contextual data. Contextual data may be in the form of a histogram, a tabular format, or descriptions or definition of KPIs, or may be in other formats of display. The contextual data may also include recommendations of actions to be performed based on the contextual data. The recommendations of actions may be in the form of a text display notifying the user or actions to be performed. The recommendations of actions may also be a link or a button to an action. The user may interact with the link or the button and the actions may be performed. The contextual data may also be created by various machine learning algorithms. The machine learning algorithms may be trained by test or sample metric values and may create contextual data based on the data fields selected by the user. The formats of display may be preconfigured by the server 125. Alternatively the user may be able to reconfigure the formats of display or create new formats of display based on a preference of the user. Data may be displayed contextualizing the data field selected. A predetermined time period or data range may be displayed along with the KPI value at the particular selected data field. At step 214, important derived metrics may be calculated. Derived metrics may be related to the ranking of the data elements displayed on the electronic data card. For example, if the user selects the revenue of ACME company as the KPI, then derived metrics regarding the revenue may be calculated to determine the total count of similar companies, the revenue of the similar companies, the top and bottom of all the revenues, and the ranking of the revenue of ACME among the similar companies. Similar companies may be automatically determined by goods and/or services offered by the companies, or by the category of the companies, or by the size of the companies (e.g., revenue or number of employees), or may be manually selected by the user. At step 215, upon creation of the contextual data and the calculation of the derived metrics, the contextual data and the derived metrics may be used to create a display interface (e.g., a graphic display interface). At step 216, the display interface may be presented to the user for view of contextual data. Upon viewing the display interface the user may be able to adjust the size of the display interface (e.g., making the display interface bigger or smaller). The size of the display interface may be adjusted using a mouse (e.g., dragging the display bigger or smaller), or by using a keyboard and/or a mouse wheel, or by using gesture (e.g., pinch). Adjusting the size of the display interface may also adjust the size of text within the display interface and/or adjust the density of information displayed in the display interface. For example, as the user increase the size of the display interface, the display size of the text within the display interface may scale up accordingly, thereby improving the legibility of the information displayed in the display interface. Alternatively or in combination, as the user increase the size of the display interface the amount of information may also increase accordingly. For example, as the size of display interface increases the scale on both the x axis and y axis may display more data or display data in more granular fashion. Further description of the content enrichment feature are presented in connection with FIGS. 3A and 3B below.

In addition to, or separately from the selection of the content enrichment feature, the metric trending analysis feature may be selected at step 220. At step 221, an electronic data card may be requested by the user, and the electronic data card may contain metric values in one or more electronic data card elements. At step 222, a determination may be made to determine if saved metric values exist for the requested electronic data card. The saved metric values may correspond to metric values from a prior time that the electronic data card was accessed by the user, or may correspond to metric values from a predetermined time period before the current time of access, or may correspond to a time frame selected by the user or an author of the electronic data card. At step 223, if saved metric values exist for the requested electronic data card, then the saved metric values may be accessed and compared to the current metric values on the requested electronic data card and differences between the saved metric values and current metric values may be calculated. The calculated differences may be shown as trending values and may be calculated as a percentage value, or a numerical value. At step 224, the current metric values may be stored for access for future comparisons. The metric values may be stored locally on the user device 101 or may be stored on the server 125. The steps 221-224 may be repeated for every instances of metric trending analysis feature. The metric values may be saved by overriding the previous saved metric value, or each metric value may be saved individually and may represent the trending data over a period of time. At step 225, the requested electronic data card may be displayed with the calculated trending values. The trending values may be represented by different color coding (e.g., red for a decrease in trending value and green for increase in trending value). The trending values may also be represented by symbols (e.g., down arrow for decrease in trending value and up arrow for increase in trending value.)

Additionally, the data masking feature may be selected at step 230. Upon selection of the data masking feature, at step 231 a determination is made based on the data contained in the electronic data card for an indication of data masking protection. Data masking protection may be the function of obfuscating, blurring, or other manipulation of the display of data to make the data unintelligible to prevent unauthorized access. Data masking protection may be applied at the data field level, or at the individual data level. For example, address may be a data field on an electronic data card, and the address data field may be configured to have data masking protection applied. Therefore, any address that may appear in the address data field may be masked to prevent unauthorized access. Alternatively, an individual address data (e.g., 123 Main St.) may be configured to have data masking protection applied. Therefore, every instance of appearance of the individual address data may be masked to prevent unauthorized access no matter which data field on the electronic data card the individual address data may appear in. At step 232, the electronic data card with the masked data may be rendered and displayed to the user. At step 233, a request may be received from the user to unmask the masked data. The request may be submitted by a specific action on the electronic data card, such as interacting with an user interface element. At step 234 the user permission setting may be requested from the user to validate authorization for the user to unmask the masked data. The user permission setting may be a login name and password, a pin number, biometric data, or may be a request to a data manager for permission to access the data. At step 235, upon validation that the user is authorized to view the data, the masked data may have the data masked protection removed and the data displayed as intelligible data.

In one embodiment, steps 231, 233 and 234 may be performed on the server 125 and the generated electronic data card may be transmitted to the user device 101. In another embodiment, steps 231-235 may all be performed on the user device 101. Generally speaking, all techniques discussed herein may be performed on at least one user device 101, and such techniques may be partially or entirely performed on at least one server 125.

Figure 3A:
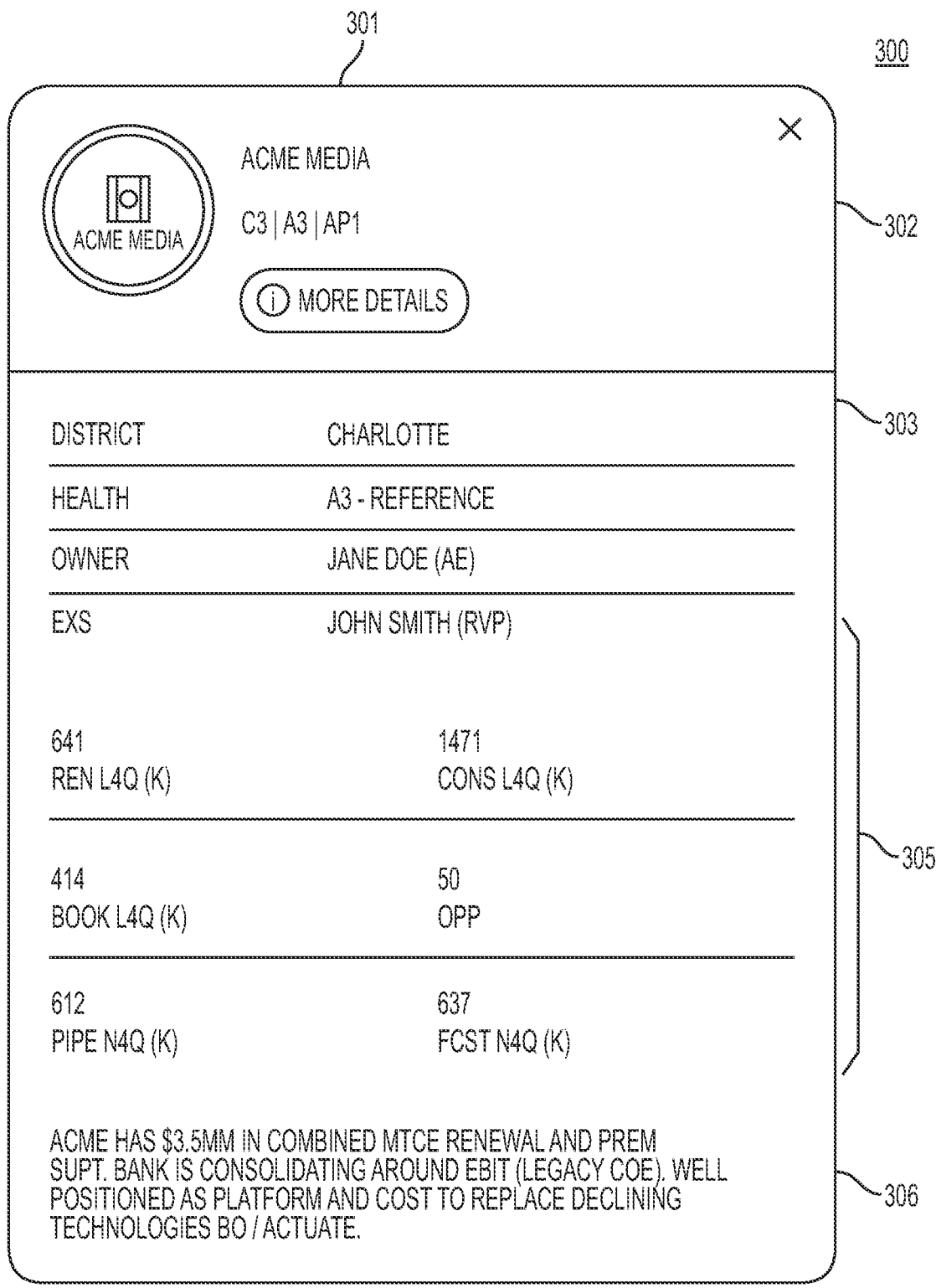
FIGS. 3A and 3B depict exemplary user interface for content enrichment feature and metric trending analysis feature, according to one aspect of the present disclosure.
Figure 3B:
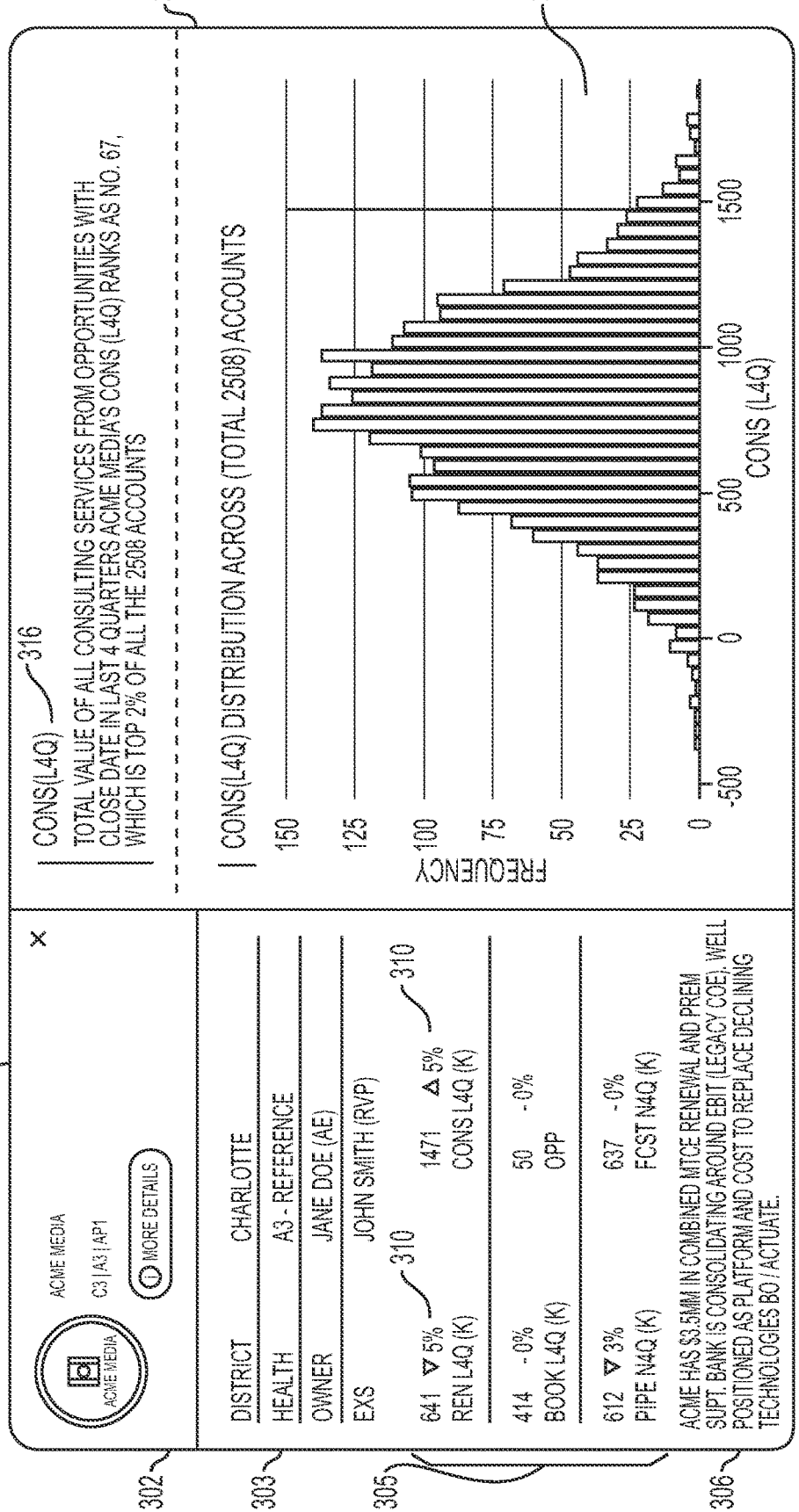

FIGS. 3A and 3B depict exemplary user interface 300 for content enrichment features and metric trending analysis features, according to one aspect of the present disclosure. FIG. 3A may be an exemplary interface of an electronic data card 301. The electronic data card 301 may include header 302, body 303, metric value(s) 305, and footer 306. Header 302 may contain data related to the name and picture of the entity of the electronic data card. Body 303 may contain information related to the entity of the electronic data card. For example, if the entity is a company, body 303 may contain the owner of the company, the address of the company, and other information. Metric values 305 may contain metric data related to the entity. Metric data may include any quantifiable information related to the entity. For example, metric data may contain metric values regarding revenue, budget, number of employee, etc. Footer 306 may contain any information related to the entity that does not belong in one of the other portion of the electronic data card.

FIG. 3B may be an exemplary interface of an electronic data card 301 with content enrichment and metric trending analysis enabled. The electronic data card 301 may include header 302, body 303, metric values 305, and footer 306 as described in FIG. 3A. The electronic data card 301 may also include metric trending display 310 and a data enrichment window 315. The metric trending display 310 may display the data trends after comparing the current metric values with saved metric values. For example, the current metric value for Renew of last four quarters (REN L4Q) (K) is 641, which has decreased by 5% from the previous value, as indicated by the down arrow. Data enrichment window 315 may include definition 316 and contextual display 317. While the contextual display 317 depicted in FIG. 3B is a histogram, any other contextual display, such as a pie chart/graph or tabular chart/graph may also be displayed. Data enrichment window 315 may be displayed when the user selects a data field with a pointing device or by performing a gesture. The user may also hover the point device over a data field to invoke the data enrichment window 315. As shown in exemplary FIG. 3B, the user has selected the data field Consulting of last four quarters (CONS L4Q) for data enrichment. The definition 316 may then display the definition of the data field "CONS L4Q" and contextual display 317 may display the element within the data field as a histogram. The contextual display 317 displays the metric value "1471" of the "CONS L4Q" data field as a distribution across total accounts, thereby providing user with contextual understanding of the data elements.

Figures 4A, 4B:
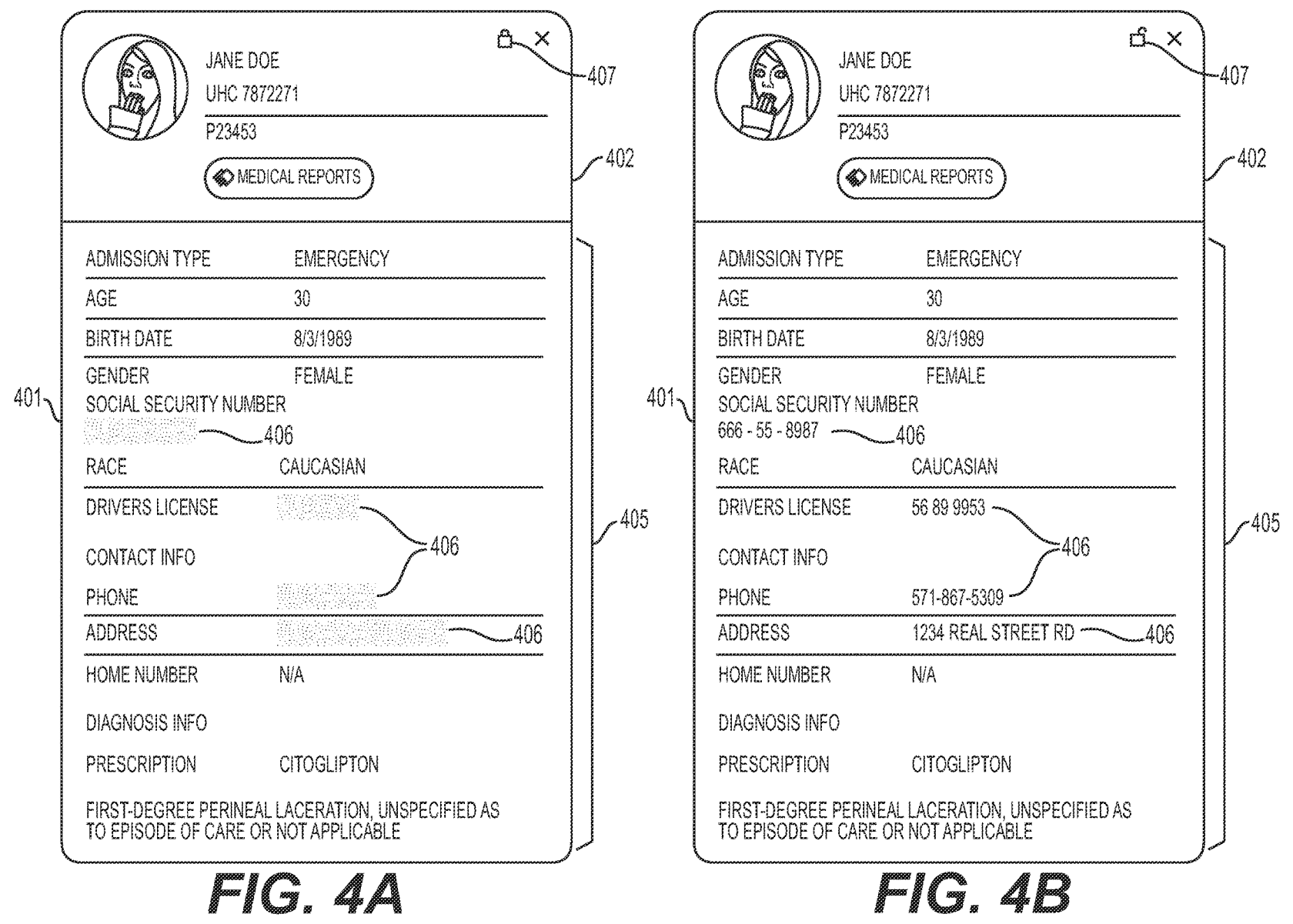

FIGS. 4A and 4B depict exemplary user interfaces for data masking features, according to one aspect of the present disclosure. FIG. 4A may be an exemplary interface of an electronic data card 401 with data masking features enabled. The electronic data card 401 may include header 402, body 405, masked data 406, and data masking protection toggle 407. Header 402 may contain data related to the name and picture of the entity of the electronic data card. Body 405 may contain data regarding the entity and may include masked data 406 to prevent unauthorized access of the sensitive data. Masked data 406 may be any personally identifiable information (PII) such as social security number, driver's license number, telephone number, address, etc. Masked data 406 may also be other sensitive data, such as salary, job description, or any other data that warrants protection from unauthorized access. Exemplary electronic data card 401 may be a data card regarding the medical records of a patient, and may be depicted in FIG. 4A as displayed with data masking protection applied. As depicted by masked data 406, the sensitive data is masked to prevent unauthorized access. If the user wants to view the sensitive data, the user may interact with the data masking protection toggle 407 to disable data masking protection. Upon interacting with the data masking protection toggle 407, the authorization level of the user may be checked to determine if the user has the proper authorization to view the sensitive data unmasked. If the user does not have the proper authorization level, then the user may be requested to enter validation information to gain proper authorization level. Validation information may be login name and password, a pin number, or biometric data, or other authentication information.

FIG. 4B may be an exemplary interface of an electronic data card 401 with data masking feature disabled. Upon authentication or validation of the authorization level of the user, the data masking protection toggle 407 may update to reflect that the data masking feature has been disabled. Masked data 406 may also update to unmask the sensitive data by displaying the sensitive data in an intelligible format. After viewing the sensitive data, the user may enable the data masking protection by interacting with the data masking protection toggle 407.

Figure 5:
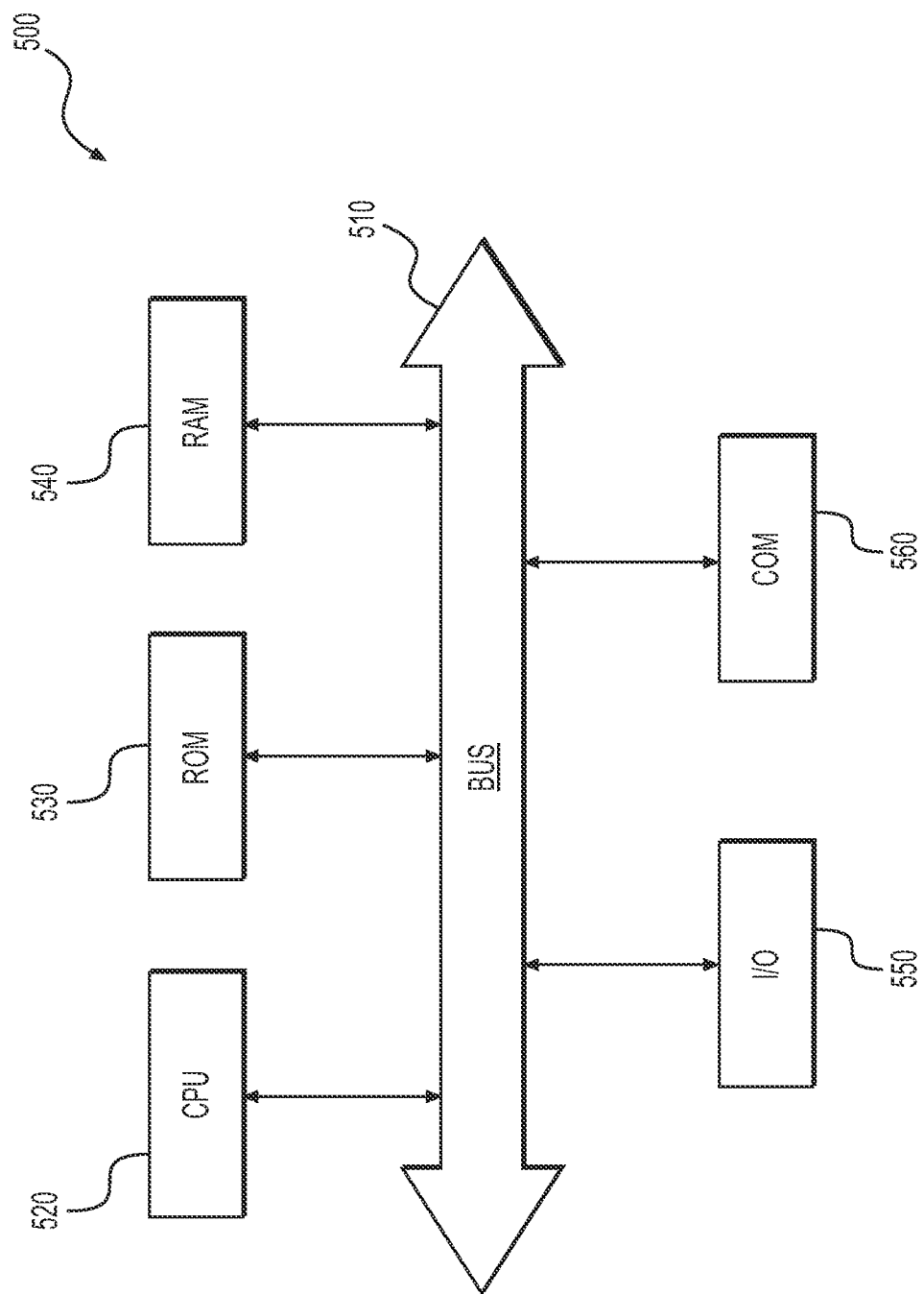
FIG. 5 depicts an exemplary computer device or system in which embodiments of the present disclosure, or portions thereof, may be implemented.

FIG. 5 depicts a high-level functional block diagram of an exemplary computer device or system, in which embodiments of the present disclosure, or portions thereof, may be implemented, e.g., as computer-readable code. Additionally, each of the exemplary computer servers, databases, user interfaces, modules, and methods described above with respect to FIGS. 1-4 can be implemented in device 500 using hardware, software, firmware, tangible computer readable media having instructions stored thereon, or a combination thereof and may be implemented in one or more computer systems or other processing systems. Hardware, software, or any combination of such may implement each of the exemplary systems, user interfaces, and methods described above with respect to FIGS. 1-4.

If programmable logic is used, such logic may be executed on a commercially available processing platform or a special purpose device. One of ordinary skill in the art may appreciate that embodiments of the disclosed subject matter can be practiced with various computer system configurations, including multi-core multiprocessor systems, minicomputers, mainframe computers, computers linked or clustered with distributed functions, as well as pervasive or miniature computers that may be embedded into virtually any device.

For instance, at least one processor device and a memory may be used to implement the above-described embodiments. A processor device may be a single processor or a plurality of processors, or combinations thereof. Processor devices may have one or more processor "cores."

Various embodiments of the present disclosure, as described above in the examples of FIGS. 1-4, may be implemented using device 500. After reading this description, it will become apparent to a person skilled in the relevant art how to implement embodiments of the present disclosure using other computer systems and/or computer architectures. Although operations may be described as a sequential process, some of the operations may in fact be performed in parallel, concurrently, and/or in a distributed environment, and with program code stored locally or remotely for access by single or multi-processor machines. In addition, in some embodiments the order of operations may be rearranged without departing from the spirit of the disclosed subject matter.

As shown in FIG. 5, device 500 may include a central processing unit (CPU) 520. CPU 520 may be any type of processor device including, for example, any type of special purpose or a general-purpose microprocessor device. As will be appreciated by persons skilled in the relevant art, CPU 520 also may be a single processor in a multi-core/multi-processor system, such system operating alone, or in a cluster of computing devices operating in a cluster or server farm. CPU 520 may be connected to a data communication infrastructure 510, for example, a bus, message queue, network, or multi-core message-passing scheme.

Device 500 also may include a main memory 540, for example, random access memory (RAM), and also may include a secondary memory 530. Secondary memory 530, e.g., a read-only memory (ROM), may be, for example, a hard disk drive or a removable storage drive. Such a removable storage drive may comprise, for example, a floppy disk drive, a magnetic tape drive, an optical disk drive, a flash memory, or the like. The removable storage drive in this example reads from and/or writes to a removable storage unit in a well-known manner. The removable storage unit may comprise a floppy disk, magnetic tape, optical disk, etc., which is read by and written to by the removable storage drive. As will be appreciated by persons skilled in the relevant art, such a removable storage unit generally includes a computer usable storage medium having stored therein computer software and/or data.

In alternative implementations, secondary memory 530 may include other similar means for allowing computer programs or other instructions to be loaded into device 500. Examples of such means may include a program cartridge and cartridge interface (such as that found in video game devices), a removable memory chip (such as an EPROM, or PROM) and associated socket, and other removable storage units and interfaces, which allow software and data to be transferred from a removable storage unit to device 500.

Device 500 also may include a communications interface ("COM") 560. Communications interface 560 allows software and data to be transferred between device 500 and external devices. Communications interface 560 may include a modem, a network interface (such as an Ethernet card), a communications port, a PCMCIA slot and card, or the like. Software and data transferred via communications interface 560 may be in the form of signals, which may be electronic, electromagnetic, optical, or other signals capable of being received by communications interface 560. These signals may be provided to communications interface 560 via a communications path of device 500, which may be implemented using, for example, wire or cable, fiber optics, a phone line, a cellular phone link, an RF link or other communications channels.

The hardware elements, operating systems and programming languages of such equipment are conventional in nature, and it is presumed that those skilled in the art are adequately familiar therewith. Device 500 also may include input and output ports 550 to connect with input and output devices such as keyboards, mice, touchscreens, monitors, displays, etc. Of course, the various server functions may be implemented in a distributed fashion on a number of similar platforms, to distribute the processing load. Alternatively, the servers may be implemented by appropriate programming of one computer hardware platform.

It should be appreciated that in the above description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description are hereby expressly incorporated into this Detailed Description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those skilled in the art. For example, in the following claims, any of the claimed embodiments can be used in any combination.

Thus, while certain embodiments have been described, those skilled in the art will recognize that other and further modifications may be made thereto without departing from the spirit of the invention, and it is intended to claim all such changes and modifications as falling within the scope of the invention. For example, functionality may be added or deleted from the block diagrams and operations may be interchanged among functional blocks. Steps may be added or deleted to methods described within the scope of the present invention.

The above disclosed subject matter is to be considered illustrative, and not restrictive, and the appended claims are intended to cover all such modifications, enhancements, and other implementations, which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description. While various implementations of the disclosure have been described, it will be apparent to those of ordinary skill in the art that many more implementations and implementations are possible within the scope of the disclosure. Accordingly, the disclosure is not to be restricted except in light of the attached claims and their equivalents.

What is claimed is:

1. A computer-implemented method for electronic data card enhancements, the method comprising:
   requesting, by one or more processors, at least one electronic data card containing data within a plurality of data elements;
   determining, by the one or more processors, at least one value adding feature applicable to the data, the at least one value adding feature comprising a content enrichment feature;

applying, by the one or more processors, the at least one value adding feature to the data;

presenting, by the one or more processors, the at least one electronic data card containing data and the applied at least one value adding feature of the data;

displaying, by the one or more processors, the at least one electronic data card comprising data elements within a plurality of data fields;

detecting, by the one or more processors, a selection of at least one of the plurality of data fields;

creating, by the one or more processors, contextual data from values of the data elements in the selected at least one of the plurality of data fields, the contextual data comprising a definition of a key performance indicator (KPI) displayed in the selected at least one of the plurality of data fields or a recommendation generated by a machine learning algorithm of an action to be performed; and calculating, by the one or more processors, derived metrics from the contextual data.

2. The computer-implemented method of claim 1, wherein the at least one value adding feature further comprises a metric trending analysis feature and/or data a masking feature.

3. The computer-implemented method of claim 1, the method further comprising:

creating, by the one or more processors, a graphic display interface based on the contextual data and the derived metrics; and displaying, by the one or more processors, the graphic display interface proximate to the electronic data card.

4. The computer-implemented method of claim 3, wherein the graphic display interface is at least one of a histogram, pie chart, and/or tabular chart.

5. The computer-implemented method of claim 2, wherein the value adding feature further comprises a metric trending analysis feature, and further comprising:

checking, by the one or more processors, for existence of saved metric values for the requested electronic data card;

comparing, by the one or more processors, the saved metric values with current metric values;

saving, by the one or more processors, the current metric values as saved metric values; and displaying, by the one or more processors, based on the comparing, a difference between the saved metric values and the current metric values.

6. The computer-implemented method of claim 2, wherein determining the value adding feature further comprises the data masking feature, and further comprising:

checking, by the one or more processors, at least one electronic data card property for masking protection settings;

rendering, by the one or more processors, the electronic data card with masked data based on the masking protection settings;

receiving, by the one or more processors, a request to unmask the masked data from a user;

receiving, by the one or more processors, authentication information from the user; and displaying, by the one or more processors, the unmasked data based on the received authentication information from the user.

7. The computer-implemented method of claim 6, wherein the authentication information is at least one of a password, a pin number, biometric data, and/or permission settings.

8. A computer system for electronic data card enhancements, the computer system comprising:

at least one memory having processor-readable instructions stored therein; and at least one processor configured to access the memory and execute operations, the operations comprising:

requesting at least one electronic data card containing data within a plurality of data elements;

determining at least one value adding feature applicable to the data, the at least one value adding feature comprising a content enrichment feature;

applying the at least one value adding feature to the data;

presenting the at least one electronic data card containing data and the applied at least one value adding feature of the data;

displaying the at least one electronic data card comprising data elements within a plurality of data fields;

detecting a selection of at least one of the plurality of data fields;

creating contextual data from values of the data elements in the selected at least one of the plurality of data fields, the contextual data comprising a definition of a key performance indicator (KPI) displayed in the selected at least one of the plurality of data fields or a recommendation generated by a machine learning algorithm of an action to be performed; and calculating derived metrics from the contextual data.

9. The computer system of claim 8, wherein the at least one value adding feature further includes at least one of metric trending analysis feature and/or data masking feature.

10. The computer system of claim 8, the operations further include:

creating a graphic display interface based on the contextual data and the derived metrics; and displaying the graphic display interface proximate to the electronic data card.

11. The computer system of claim 10, wherein the graphic display interface is at least one of a histogram, pie chart, and/or tabular chart.

12. The computer system of claim 9, wherein determining the at least one value adding feature further includes selecting the metric trending analysis feature, and further includes functions for:

checking for existence of saved metric values for the requested electronic data card;

comparing the saved metric values with current metric values;

saving the current metric values as saved metric values; and displaying based on the comparing, a difference between the saved metric values and the current metric values.

13. The computer system of claim 9, wherein determining the at least one value adding feature further includes selecting the data masking feature, and further includes functions for:

checking at least one electronic data card property for masking protection settings;

rendering the electronic data card with masked data based on the masking protection settings;

receiving a request to unmask the masked data from a user;

receiving authentication information from the user; and displaying the unmasked data based on the received authentication information from the user.

14. The computer system of claim 13, wherein the authentication information is at least one of, a password, a pin number, biometric data, and/or permission settings.

15. A non-transitory computer-readable medium comprising instructions for electronic data card enhancements, the non-transitory computer-readable medium storing instructions that, when executed by at least one processor, configure the at least one processor to perform operations comprising:
- requesting, by one or more processors, at least one electronic data card containing data within a plurality of data elements;
- determining, by the one or more processors, at least one value adding feature applicable to the data, the at least one value adding feature comprising a content enrichment feature;
- applying, by the one or more processors, the at least one value adding feature to the data;
- presenting, by the one or more processors, the at least one electronic data card containing data and the applied at least one value adding feature of the data;
- displaying, by the one or more processors, the at least one electronic data card comprising data elements within a plurality of data fields;
- detecting, by the one or more processors, a selection of at least one of the plurality of data fields;
- creating, by the one or more processors, contextual data from values of the data elements in the selected at least one of the plurality of data fields, the contextual data comprising a definition of a key performance indicator (KPI) displayed in the selected at least one of the plurality of data fields or a recommendation generated by a machine learning algorithm of an action to be performed; and
- calculating, by the one or more processors, derived metrics from the contextual data.

16. The non-transitory computer-readable medium of claim 15, wherein the at least one value adding feature further includes at least one of metric trending analysis feature and/or data masking feature.

17. The non-transitory computer-readable medium of claim 16, wherein the operations further include:
- creating, by the one or more processors, a graphic display interface based on the contextual data and the derived metrics; and
- displaying, by the one or more processors, the graphic display interface proximate to the electronic data card.

18. The non-transitory computer-readable medium of claim 17, wherein the graphic display interface is at least one of a histogram, pie chart, and/or tabular chart.

19. The non-transitory computer-readable medium of claim 16, wherein determining the at least one value adding feature further includes selecting the metric trending analysis feature, and further include:
- checking, by the one or more processors, for existence of saved metric values for the requested electronic data card;
- comparing, by the one or more processors, the saved metric values with current metric values;
- saving, by the one or more processors, the current metric values as saved metric values; and
- displaying, by the one or more processors, based on the comparing, a difference between the saved metric values and the current metric values.

20. The non-transitory computer-readable medium of claim 16, wherein determining the at least one value adding feature further includes selecting the data masking feature, and further include:
- checking, by the one or more processors, at least one electronic data card property for masking protection settings;
- rendering, by the one or more processors, the electronic data card with masked data based on the masking protection settings;
- receiving, by the one or more processors, a request to unmask the masked data from a user;
- receiving, by the one or more processors, authentication information from the user; and
- displaying, by the one or more processors, the unmasked data based on the received authentication information from the user.

* * * * *